(12) United States Patent
Adriaens et al.

(10) Patent No.: US 10,864,354 B2
(45) Date of Patent: Dec. 15, 2020

(54) HYDRAULIC AUTO CROSSING BALLOON/CATHETER

(71) Applicants: Boston Scientific Scimed Inc., Maple Grove, MN (US); Mayo Foundation for Medical Education and Research, Rochester, MN (US)

(72) Inventors: Joseph E. Adriaens, Elk River, MN (US); Douglas D. Pagoria, Forest Lake, MN (US); Joel T. Eggert, Plymouth, MN (US); James P. Rohl, Prescott, WI (US); Roger W. McGowan, Ostego, MN (US); Katherine L. Baldwin, Apple Valley, MN (US); Todd College, Little Canada, MN (US); James K. Cawthra, Jr., Ramsey, MN (US); Eric M. Petersen, Maple Grove, MN (US); James A. Klos, Bay City, WI (US); Douglas Pennington, Stillwater, MN (US)

(73) Assignees: Boston Scientific Scimed Inc, Maple Grove, MN (US); Mayo Foundation for Medical Education and Research, Rochester, MN (US)

(*) Notice: Subject to any disclaimer, the term of this patent is extended or adjusted under 35 U.S.C. 154(b) by 433 days.

(21) Appl. No.: 15/814,851

(22) Filed: Nov. 16, 2017

(65) Prior Publication Data
US 2018/0133442 A1 May 17, 2018

Related U.S. Application Data

(60) Provisional application No. 62/423,556, filed on Nov. 17, 2016.

(51) Int. Cl.
*A61M 25/10* (2013.01)
*A61M 25/06* (2006.01)
*A61M 25/01* (2006.01)
*A61M 29/02* (2006.01)
(Continued)

(52) U.S. Cl.
CPC ..... *A61M 25/1002* (2013.01); *A61B 17/3478* (2013.01); *A61M 25/0108* (2013.01);
(Continued)

(58) Field of Classification Search
CPC .......... A61M 25/1002; A61M 25/0606; A61M 29/02; A61M 25/1018; A61M 25/06;
(Continued)

(56) References Cited

U.S. PATENT DOCUMENTS 4,465,072 A * 8/1984 Taheri ............... A61B 17/22
600/569
4,802,479 A * 2/1989 Haber ............... A61B 17/3468
128/DIG. 25
(Continued)

FOREIGN PATENT DOCUMENTS

| JP | 2014-503246 A | 2/2014 |
| WO | 2008073852 A2 | 6/2008 |
| WO | 2014097301 A1 | 6/2014 |

OTHER PUBLICATIONS

International Search Report and Written Opinion issued in PCT/US2017/061987, dated Mar. 13, 2018, 11 pages.

*Primary Examiner* — Julian W Woo
(74) *Attorney, Agent, or Firm* — Faegre Drinker Biddle & Reath LLP (57) ABSTRACT

Apparatuses, systems, and methods for crossing a tissue region may include a catheter and a tip section arranged therewith. The tip section may be configured to puncture the tissue region and create an opening therein, dilate the opening in the tissue region, and pass through the opening.

20 Claims, 7 Drawing Sheets

(51) Int. Cl.
 *A61B 17/34* (2006.01)
 *A61B 17/00* (2006.01)
 *A61M 25/09* (2006.01)

(52) U.S. Cl.
 CPC ........ *A61M 25/06* (2013.01); *A61M 25/0606* (2013.01); *A61M 25/1018* (2013.01); *A61M 29/02* (2013.01); *A61B 2017/00247* (2013.01); *A61B 2017/3486* (2013.01); *A61B 2017/3488* (2013.01); *A61M 25/104* (2013.01); *A61M 2025/0687* (2013.01); *A61M 2025/09008* (2013.01)

(58) Field of Classification Search
 CPC ...... A61M 25/0108; A61M 2025/0687; A61M 2025/09008; A61M 25/104; A61B 17/3478; A61B 2017/3488; A61B 2017/3486; A61B 2017/00247
 See application file for complete search history.

(56) References Cited

U.S. PATENT DOCUMENTS

| | | | |
|---|---|---|---|
| 5,702,367 A * | 12/1997 | Cover | A61M 25/0606 604/110 |
| 5,957,941 A | 9/1999 | Ream | |
| 5,997,509 A * | 12/1999 | Rosengart | A61K 48/00 604/164.01 |
| 6,063,056 A * | 5/2000 | Engelberg | A61M 25/10 604/97.01 |
| 6,109,264 A * | 8/2000 | Sauer | A61M 16/0472 128/200.26 |
| 6,692,458 B2 * | 2/2004 | Forman | A61M 25/0084 604/101.03 |
| 7,056,294 B2 | 6/2006 | Khairkhahan et al. | |
| 7,763,043 B2 | 7/2010 | Goodin et al. | |
| 7,766,878 B2 | 8/2010 | Tremaglio, Jr. et al. | |
| 8,308,682 B2 * | 11/2012 | Kramer | A61B 17/3478 604/96.01 |
| 8,715,169 B2 * | 5/2014 | Chang | A61B 17/12104 600/116 |
| 9,079,000 B2 | 7/2015 | Hanson et al. | |
| 9,220,532 B2 * | 12/2015 | Noda | A61B 17/3474 |
| 9,301,777 B2 * | 4/2016 | Silvestro | A61M 25/0194 |
| 9,492,190 B2 * | 11/2016 | Brannan | A61B 17/34 |
| 2002/0169377 A1 | 11/2002 | Khairkhahan et al. | |
| 2006/0135984 A1 | 6/2006 | Kramer et al. | |
| 2008/0200943 A1 | 8/2008 | Barker et al. | |
| 2011/0257723 A1 | 10/2011 | McNamara | |
| 2011/0270239 A1 | 11/2011 | Werneth | |

* cited by examiner

HYDRAULIC AUTO CROSSING BALLOON/CATHETER

CROSS-REFERENCE TO RELATED APPLICATION

This application claims priority to Provisional Application No. 62/423,556, filed Nov. 17, 2016, which is herein incorporated by reference in its entirety.

TECHNICAL FIELD

The present invention relates to medical devices and methods for accessing an anatomical space of the body. More specifically, the invention relates to apparatuses, systems, and methods for crossing a tissue region.

BACKGROUND

Intravascular catheters may be used for treating a variety of different diseases in a minimally invasive manner. Various cardiology techniques such as angioplasty, tissue ablation, and other diagnostic and therapeutic procedures may require crossing of a tissue region to reach a target diagnostic and/or therapeutic site. This may include puncturing a septal wall of the heart (or other heart tissue) to reach the left atrium of a patient.

In addition to puncturing the tissue, the diagnostic and/or therapeutic procedures may require arranging devices or other physical structures on an opposite side of the opening created in the tissue. The devices or other physical structures may be larger than the opening created, and therefore, the opening must also be dilated to execute the desired diagnostic and/or therapeutic procedure. Puncturing, dilation, and crossing may require distinct tools for each operation.

SUMMARY

In Example 1, an apparatus for crossing a tissue region, the apparatus comprising: a catheter sized and shaped for vascular access and including an elongate body extending between a proximal end and a distal end; and a tip section arranged at the distal end of the elongate body configured to puncture the tissue region and create an opening therein, dilate the opening in the tissue region, and pass through the opening.

In Example 2, the apparatus of Example 1, wherein the tip section comprises a needle portion configured to puncture the tissue region and a balloon configured to dilate the opening in the tissue region.

In Example 3, the apparatus of Example 2, wherein the needle portion is configured to retract within the tip section.

In Example 4, the apparatus of Example 2, wherein the balloon comprises a first section and a second section, and the first section of the balloon is configured to inflate.

In Example 5, the apparatus of Example 4, wherein at least a portion of the first section of the balloon comprises a first diameter and the second section of the balloon comprises a second diameter, the first diameter is less than the second diameter.

In Example 6, the apparatus of Example 5, wherein the first section tapers from the second diameter to the first diameter.

In Example 7, the apparatus of any of Examples 4-6, wherein the second section of the balloon is coupled to a portion of the tip section.

In Example 8, the apparatus of any of Examples 2-7, wherein the balloon is configured to inflate to a substantially spherical shape in a first configuration to dilate the opening in the tissue region.

In Example 9, the apparatus of any of Examples 2-8, wherein the balloon is configured to asymmetrically inflate.

In Example 10, the apparatus of any of Examples 2-7, wherein the balloon is configured to pass at least a portion of the tip section from a first side of the tissue region to a second side of the tissue region in response to inflation thereof, with the first side being opposite the second side.

In Example 11, the apparatus of any of Examples 1-10, wherein the tip section comprises an aperture configured to pass a guidewire therethrough.

In Example 12, the apparatus of any of Examples 1-11, wherein the tip section comprises a first tip section having a first tip section diameter and a second tip section having a second tip section diameter, and the first tip section diameter is less than the second tip section diameter.

In Example 13, the apparatus of Example 12, further comprising a visualization element arranged at a distal end of the second tip section.

In Example 14, the apparatus of any of Examples 12-13, further comprising a radiopaque marker arranged approximately at a transition between the first tip section and the second tip section.

In Example 15, the apparatus of any of Examples 1-15, further comprising a hydraulic actuator configured to assist in passing the tip section through the opening in the tissue region.

In Example 16, an apparatus for crossing a tissue region, the apparatus comprising: a catheter sized and shaped for vascular access and including an elongate body extending between a proximal end and a distal end; and a tip section arranged at the distal end of the elongate body, the tip section including: a needle portion arranged at a distal end of the tip section and configured to puncture the tissue region to create an opening therein, and a balloon arranged proximally of the needle portion and configured to dilate the opening in the tissue region and pass the tip section through the opening.

In Example 17, the apparatus of Example 16, wherein the balloon comprises a first section and a second section, at least a portion of the first section of the balloon comprises a first diameter and the second section of the balloon comprises a second diameter, the first diameter is less than the second diameter.

In Example 18, the apparatus of Example 17, wherein the first section tapers from the second diameter to the first diameter.

In Example 19, the apparatus of Example 16, wherein the balloon is configured to inflate to a substantially spherical shape to dilate the opening in the tissue region.

In Example 20, the apparatus of Example 16, wherein the balloon is configured to asymmetrically inflate.

In Example 21, the apparatus of Example 20, wherein a distal portion of the balloon is configured to inflate at a greater rate than a proximal section of the balloon thereby asymmetrically inflating the balloon.

In Example 22, the apparatus of Example 16, wherein the tip section comprises a first tip section having a first tip section diameter and a second tip section having a second tip section diameter, and the first tip section diameter is less than the second tip section diameter.

In Example 23, the apparatus of Example 22, further comprising a visualization element arranged at a distal end of the second tip section.

In Example 24, the apparatus of Example 22, further comprising a radiopaque marker arranged approximately at a transition between the first tip section and the second tip section.

In Example 25, the apparatus of Example 16, further comprising a hydraulic actuator configured to assist in passing the tip section through the opening in the tissue region.

In Example 26, the apparatus of Example 16, wherein the balloon is configured to concurrently dilate the opening in the tissue region and pass the tip section through the opening.

In Example 27, an apparatus for crossing a tissue region, the apparatus comprising: a catheter sized and shaped for vascular access and including an elongate body extending between a proximal end and a distal end; a tip section arranged at the distal end of the elongate body, the tip section including: a needle portion arranged at a distal end of the tip section and configured to puncture the tissue region in a first configuration to create an opening therein and retract within the tip section in a second configuration, and a balloon arranged proximally of the needle portion and configured to dilate the opening in the tissue region and pass a portion of the tip section through the opening while in a partially inflated configuration; and a hydraulic actuator coupled to a distal end of the catheter and configured to drive the needle portion through the tissue region and assist in the balloon passing the tip section through the opening.

In Example 28, the apparatus of Example 27, wherein the balloon is configured to concurrently dilate the opening in the tissue region and pass the portion of the tip section through the opening in the partially inflated configuration and transition to a fully inflated configuration after passing through the opening in the tissue.

In Example 29, the apparatus of Example 27, wherein the tip section comprises a first tip section having a first tip section diameter and a second tip section having a second tip section diameter, and the first tip section diameter is less than the second tip section diameter, and a first section of the balloon is arranged to surround the first tip section and a second section of the balloon is attached to the second tip section.

In Example 30, the apparatus of Example 29, wherein the first section of the balloon comprises a tapered diameter decreasing toward the distal end of the tip section.

In Example 31, a method for crossing a tissue region, the method comprising: arranging a tip section of a catheter on the tissue region, the catheter being sized and shaped for vascular access and including an elongate body extending between a proximal end and a distal, the tip section including a needle portion and a balloon; puncturing the tissue region using the needle portion to create an opening; advancing the balloon within the opening in the tissue region; dilating the opening in the tissue region by inflating the balloon; and passing at least a portion of the tip section through the opening in the tissue region.

In Example 32, the method of Example 31, wherein dilating the opening and passing the at least a portion of the tip section through the opening occurs concurrently with inflation of the balloon.

In Example 33, the method of Example 31, further including retracting the needle portion within the tip section prior to advancing a first section of the balloon within the tissue region.

In Example 34, the method of Example 31, wherein dilating the opening in the tissue region by inflating the balloon comprises asymmetrically inflating the balloon section.

In Example 35, the method of Example 34, wherein asymmetrically inflating the balloon comprises inflating a distal portion.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
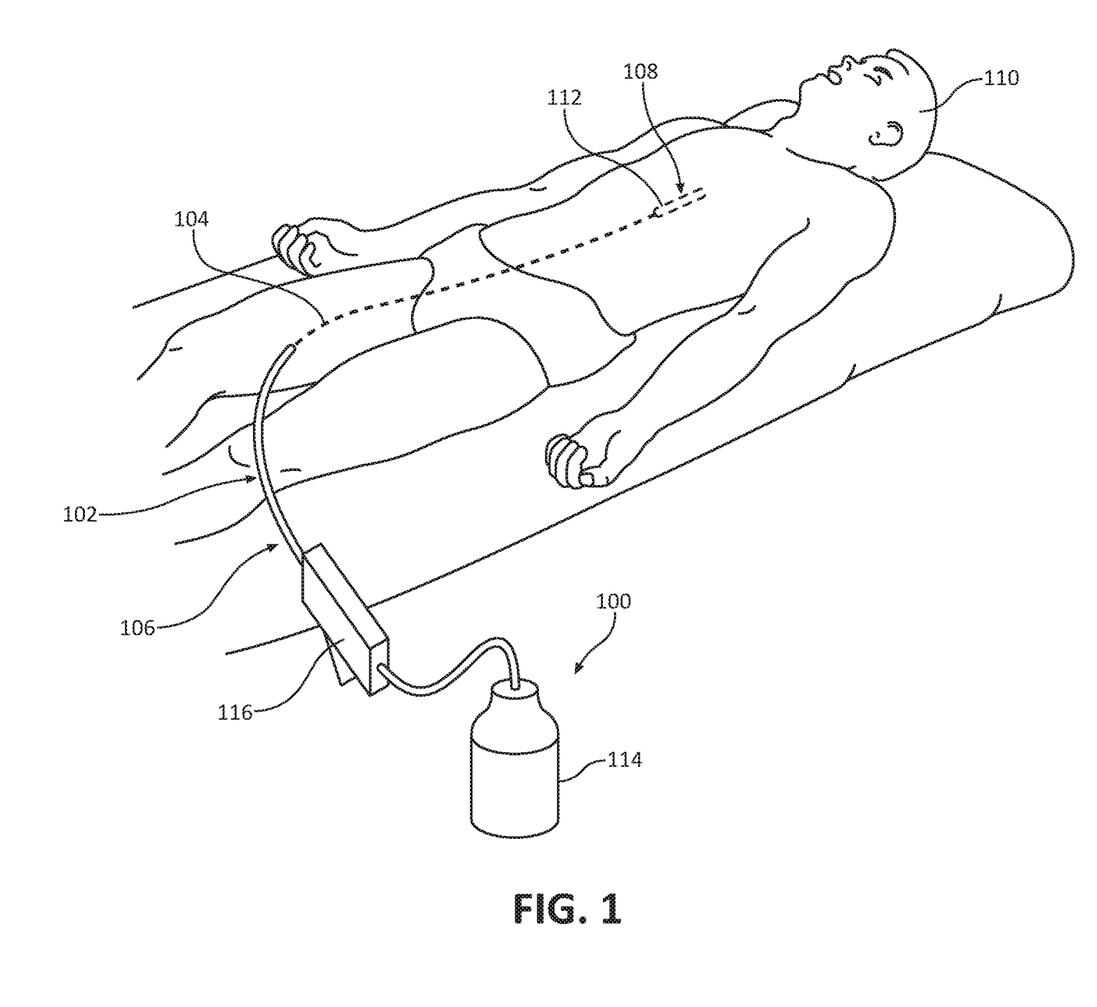
FIG. 1 shows an example apparatus for crossing a tissue region in accordance with embodiments of the disclosure.

FIG. 1 shows an example apparatus 100 for crossing a tissue region in accordance with embodiments of the disclosure. The apparatus 100 may include a catheter 102 sized and shaped for vascular access and including an elongate body 104 extending between a proximal end 106 and a distal end 108. As shown in FIG. 1, the distal end 108 of the catheter 102 is positioned at or adjacent a target location (e.g., a position within the heart) within a patient 110. The elongate body 104 may extend from an access point (e.g., the femoral artery) to the target location. The catheter 102 may be used to cross a tissue barrier such as atrial septal tissue of the heart of the patient 110, other tissue found in the heart, or other types of tissue through which an opening may be created.

Figure 2:
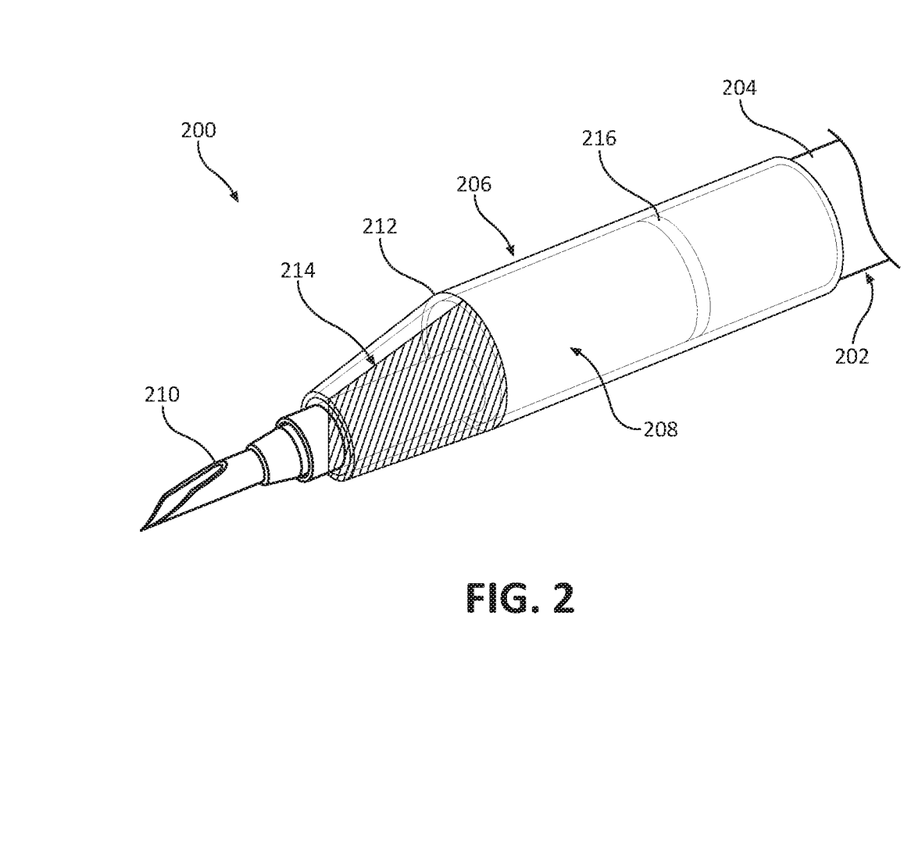
FIG. 2 shows another example apparatus for crossing a tissue region in accordance with embodiments of the disclosure.
Figure 3:
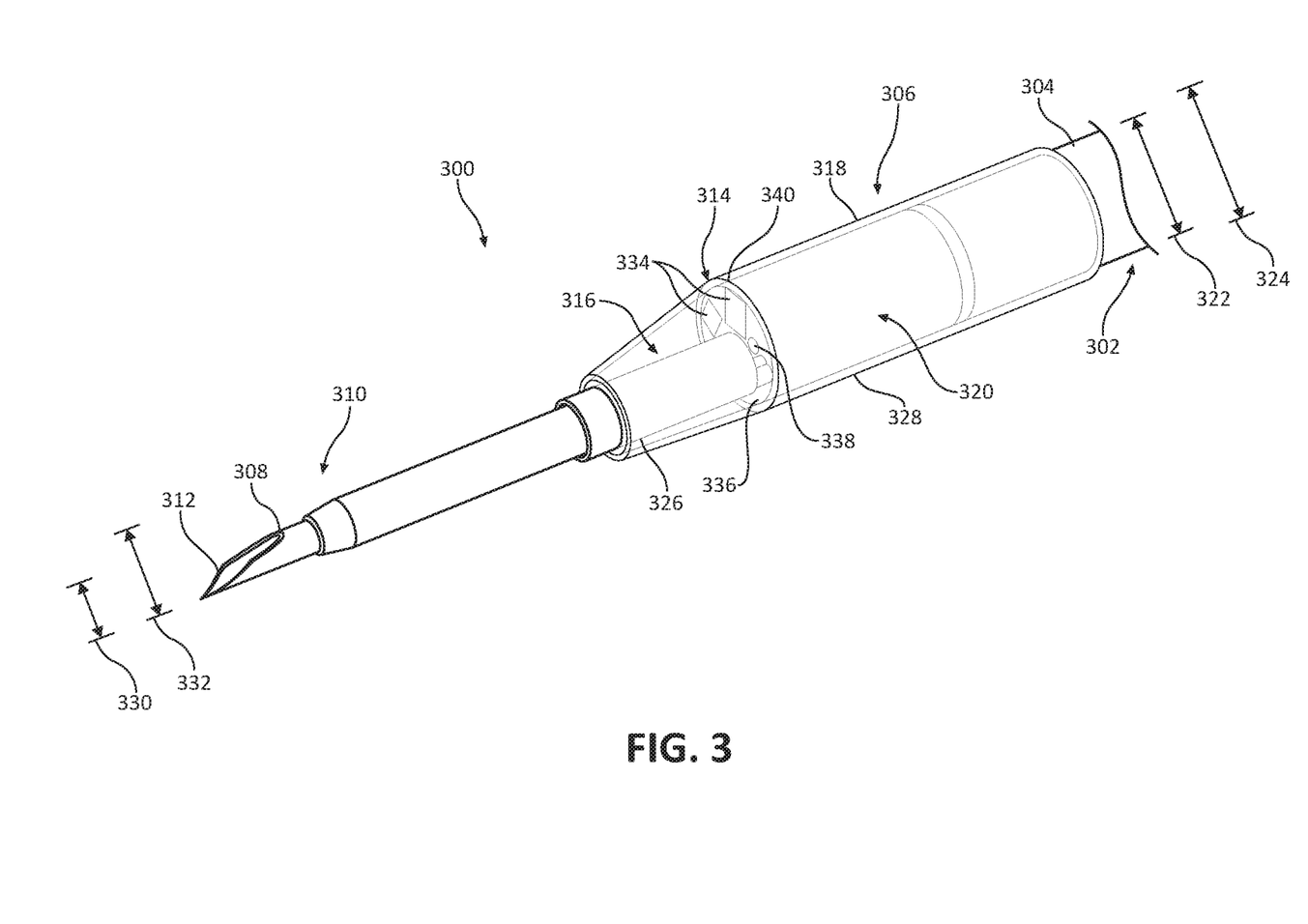
FIG. 3 shows another example apparatus for crossing a tissue region in accordance with embodiments of the disclosure.

The catheter 102 may include a tip section 112 arranged near the distal end 108 of the elongate body 104. The tip section 112 may be configured to cross the tissue barrier. In certain instances, the tip section 112 may include a balloon (e.g., as shown in FIGS. 2-4), as is described in further detail below. In order to inflate the balloon, the apparatus 100 may be coupled, at the proximal end 106, to a fluid source 114. The fluid source 114 may pump an inflation fluid (e.g., saline) through the elongate body 104 of the catheter 102 to the tip section 112. The balloon arranged with the tip section 112 may inflate in response thereto.

In certain instances, the apparatus 100 may also include a hydraulic actuator 116 that is also coupled to the proximal end 106 of the catheter 102. The hydraulic actuator 116 may be configured to move the tip section 112 forward and backward relative to the tissue region. In certain instances, the hydraulic actuator 116 may position the tip section 112 at the tissue region. In addition, the hydraulic actuator 116 may assist the tip section 112 in crossing the tissue region. The hydraulic actuator 116 may provide force to a portion of the elongate body 104 to assist in overcoming resistance from the tissue region due to the tip section 112 crossing the tissue region. In certain instances, the hydraulic actuator 116 may be a peristaltic pump or syringe filled with saline. The hydraulic action created by the hydraulic actuator 116 may be a function of inflating the balloon arranged with the tip section 112. Inflating the balloon arranged with the tip section 112 causes a hydraulic action that advances the catheter 102 distally.

FIG. 2 shows another example apparatus 200 for crossing a tissue region in accordance with embodiments of the disclosure. The apparatus 200 may include a catheter 202 that includes an elongate body 204. FIG. 2 shows a distal end portion of the elongate body 204, which may be coupled to a hydraulic actuator and/or fluid source as described above with reference to FIG. 1. The elongate body 204 may be preformed of an inert, resilient material that retains its shape and does not soften significantly at body temperature; for example, Pebax®, polyethylene, Hytrel® (polyester), or polyether ether ketone (PEEK). The elongate body 204 may be made of a variety of materials, including, but not limited to, metals and polymers. The elongate body 204 may be flexible and capable of winding through a tortuous path that leads to a target site, such as an area within the heart. The elongate body 204 may also be semi-rigid, (e.g., made of a stiff material), or by being reinforced with a coating or coil, to limit the amount of flexing.

At the distal end of the elongate body 204, the apparatus 200 may include a tip section 206. The tip section 206 may be configured to puncture the tissue region and create an opening therein, dilate the opening in the tissue region, and pass through the opening. In certain instances, the tip section 206 may include a cap tube 208 coupled to the elongate body 204. The cap tube 208 may be formed of a portion of the elongate body 204, or the cap tube 208 may be distinct from the elongate body 204. For example, the cap tube 208 may be formed to have less flexibility than the elongate body 204.

In order for the tip section 206 to puncture the tissue region, the tip section 206 may include a needle portion 210 arranged at a distal end of the tip section 206 and the elongate body 204. In addition, the tip section 206 may include a balloon 212 to both dilate an opening created by the needle portion 210, and pass the tip section 206 and the elongate body 204 through the opening. The balloon 212 may be attached (e.g., using an adhesive) or bonded (e.g., using a heat treatment) to the cap tube 208 of the tip section 206. In certain instances, the balloon 212 may extend toward the elongate body 204 and attach along a length of the cap tube 208. In addition, the balloon 212 may also be attached or bonded to the elongate body 204. The balloon 212 may be formed of a silicone, polyurethane, or another flexible polymer material. In addition, the balloon 212 may include an inflation lumen 214.

In certain instances, a portion of the cap tube 208 may taper toward the needle portion 210, as is shown in FIG. 2. The tapered portion of the cap tube 208 may be positioned within the opening subsequent to puncturing by the needle portion 210, and prior to inflation of the balloon 212. The tapered portion of the cap tube 208 may allow for the catheter 202 to partially cross the opening created by the needle portion 210 without dilation using a separate tool. The balloon 212 may subsequently be inflated to dilate the opening. In certain instances, the balloon 212 may concurrently (or cooperatively) dilate the opening and force at least a portion of the catheter 202 through the opening. The balloon 212 may similarly taper toward the needle portion 210 in certain instances, and in other instances, the balloon 212 may include a constant circumference or a substantially circular cross-section along a length thereof. Thus, the inflation lumen 214 may include a substantially circular cross-section or the inflation lumen 214 may include a tapered cross-section.

In certain instances, the catheter 202 may include a steering portion 216 arranged around a circumference thereof. The steering portion 216 may be coupled to a handle (not shown) and actuators arranged within a lumen of the elongate body 204 in order to deflect at least the tip section 206 of the catheter 202.

FIG. 3 shows another example apparatus 300 for crossing a tissue region in accordance with embodiments of the disclosure. The apparatus 300 may include a catheter 302 sized and shaped for vascular access and having an elongate body 304. FIG. 3 shows a distal end portion of the elongate body 304, which may be coupled to a hydraulic actuator and/or fluid source as described above with reference to FIG. 1. The elongate body 304 may be flexible and capable of winding through a tortuous path that leads to a target site, such as an area within the heart. The apparatus 300 may include a tip section 306 arranged at a distal end of the elongate body 304 (the portion of the catheter 302 shown in FIG. 3).

The tip section 306 may include a needle portion 308 arranged at a distal end 310 of the tip section 306. The needle portion 308 may be configured to puncture the tissue region to create an opening therein. In operation, the tip section 306 is navigated adjacent one side of the tissue region. In certain instances, the needle portion 308 may include a central aperture 312 configured to pass a guidewire therethrough. The guidewire (not shown) may assist in navigating the catheter 302 and the tip section 306 to the target site. In certain instances the catheter 302 may be an over-the-wire device that is delivered over or on a pre-placed guidewire or a delivery catheter/sheath or rapid exchange catheter may be used to assist in the insertion and placement of the catheter 302.

To create an opening, the needle portion 308 is forced against the tissue region by an operator (physician) or via a hydraulic actuator as described above with reference to FIG. 1. Once the opening is created by the needle portion 308, the distal end 310 of the tip section 306 may be forced through the opening in the tissue region. In certain instances, the needle portion 308 may be configured to retract within a portion (the distal end 310) of the tip section 306 after puncturing the tissue region. Retracting the needle portion 308 may mitigate or decrease the potential for damaging the heart on the other side of the tissue region. The needle portion 308 may be retracted within the distal end 310 of the tip section 306 prior to the distal end 310 of the tip section 306 crossing to the other side of the tissue region.

The tip section 306 may also include a balloon 314 arranged proximally of the needle portion 308. The balloon 314 may be configured to dilate the opening in the tissue region and also pass the tip section 306 through the opening. As noted above, the distal end 310 of the tip section 306 may be forced through the opening in the tissue region after the opening is created by the needle portion 308. The tip section 306 may be positioned through the opening such that at least a portion of the balloon 314 is positioned within the opening. After being positioned therein, the balloon 314 may be inflated (e.g., via a fluid source as described above with reference to FIG. 1). Inflation of the balloon 314 causes the opening created by the needle portion 308 to dilate. In addition, inflation of the balloon 314 causes at least a portion (distal of the balloon 314) of the tip section 306 to cross to the other side of the opening. Thus, the catheter 302 may include an integrated arrangement that creates an opening in tissue (via the needle portion 308), dilates the opening (via the balloon 314), and crosses the opening (via the balloon 314).

In certain instances, the balloon 314 includes a first section 316 and a second section 318, with the first section 316 of the balloon 314 being configured to inflate. All or a portion of the second section 318 of the balloon 314 may be attached, bonded, or coupled to a portion of the tip section 306 such as a cap tube 320. The cap tube 320 may be formed of a portion of the elongate body 304 of the catheter 302, or the cap tube 320 may include material that provides an attachment surface for the second section 318 of the balloon 314. In certain instances, at least a portion of the first section 316 of the balloon 314 includes a first diameter 322 and the second section 318 of the balloon 314 may include a second diameter 324. As is shown in FIG. 3, the first diameter 322 is less than the second diameter 324. As is also shown in FIG. 3, the first section 316 of the balloon 314 tapers from the second diameter 324 to the first diameter 322.

In certain instances, the balloon 314 may be configured to asymmetrically inflate. The balloon 314, for example, may be configured to inflate in a distally biased manner in order to asymmetrically inflate. As shown in FIG. 3, the first section 316 of the balloon 314 is tapered. A distal portion of the balloon 314, the portion of the first section 316 of the balloon 314 having the first diameter 322, is configured to inflate at a greater rate than a proximal section of the balloon 314, the portion of the first section 316 of the balloon 314 having the second diameter 324, thereby asymmetrically inflating the balloon 314. The taper of the first section 316 of the balloon 314 may cause the first section 316 of the balloon 314 to backfill such that a distal portion of the first section 316 of the balloon 314 fills prior to a proximal section.

The tip section 306, or more specifically the cap tube 320, may include a first tip section 326 having a first tip section diameter 330 and a second tip section 328 having a second tip section diameter 332. The first tip section 330 diameter is less than the second tip section diameter 332. The difference in diameter between the first tip section 326 and the second tip section 328 may assist in both dilating the opening created by the needle portion 308 and crossing the tip section 306 therethrough. The first tip section 326 may have a similar size to the needle portion 308. Thus, the first tip section 326 may be positioned within the opening created by the needle portion 308 without substantially forcing apart the opening.

As shown in FIG. 3, the first section 316 of the balloon 314 is arranged around a section of the first tip section 326. Thus, when the first tip section 326 is positioned within and partially through the opening created by the needle portion 308, at least a portion of the first section 316 of the balloon 314 may also be arranged within and partially through the opening. As noted above, inflation of the balloon 314 may be asymmetric whereby a distal end of the first section 316 of the balloon 314 may at a greater rate than a proximal end. As a result, the first section 316 of the balloon 314 may dilate the opening and, simultaneously, cause the first tip section 326 to cross the opening as is described in further detail with reference to FIGS. 4A-D. In certain instances, the balloon 314 may be filled using a hydraulic actuator such as a peristaltic pump or syringe filled with saline. The hydraulic action created by the hydraulic actuator may be a function of inflating the balloon 314 with the first tip section 326 being positioned within and partially through the opening created by the needle portion 308. Inflating the balloon 314, which may be asymmetric, causes a hydraulic action that advances the first tip section 326 to cross the opening. The hydraulic action automatically allows for the catheter 302 to cross the opening without need for the operator of the apparatus 300 for crossing a tissue region to push the catheter 302 through the opening.

In certain instances, the apparatus 300 may also include a visualization element 334 arranged at a distal end 336 of the second tip section 328. The visualization element 334 may include a light emitting diode (LED) or other light emitting arrangement and a camera to visualize the tissue region. In addition, the apparatus 300 may include an opening 338 arranged at the distal end 336 of the second tip section 328, coupled to a fluid source, that may be configured to fill the balloon 314. The apparatus 300 may also include a radiopaque marker 340 arranged approximately at transition between the first tip section 326 and the second tip section 328.

The illustrative components shown in FIG. 3 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 3 may be, in embodiments, integrated with various other components depicted therein (and/or components not illustrated), all of which are considered to be within the ambit of the disclosed subject matter. For example, the fluid source 114 and the hydraulic actuator 116 may be used in connection with apparatus 300.

Figure 4A:
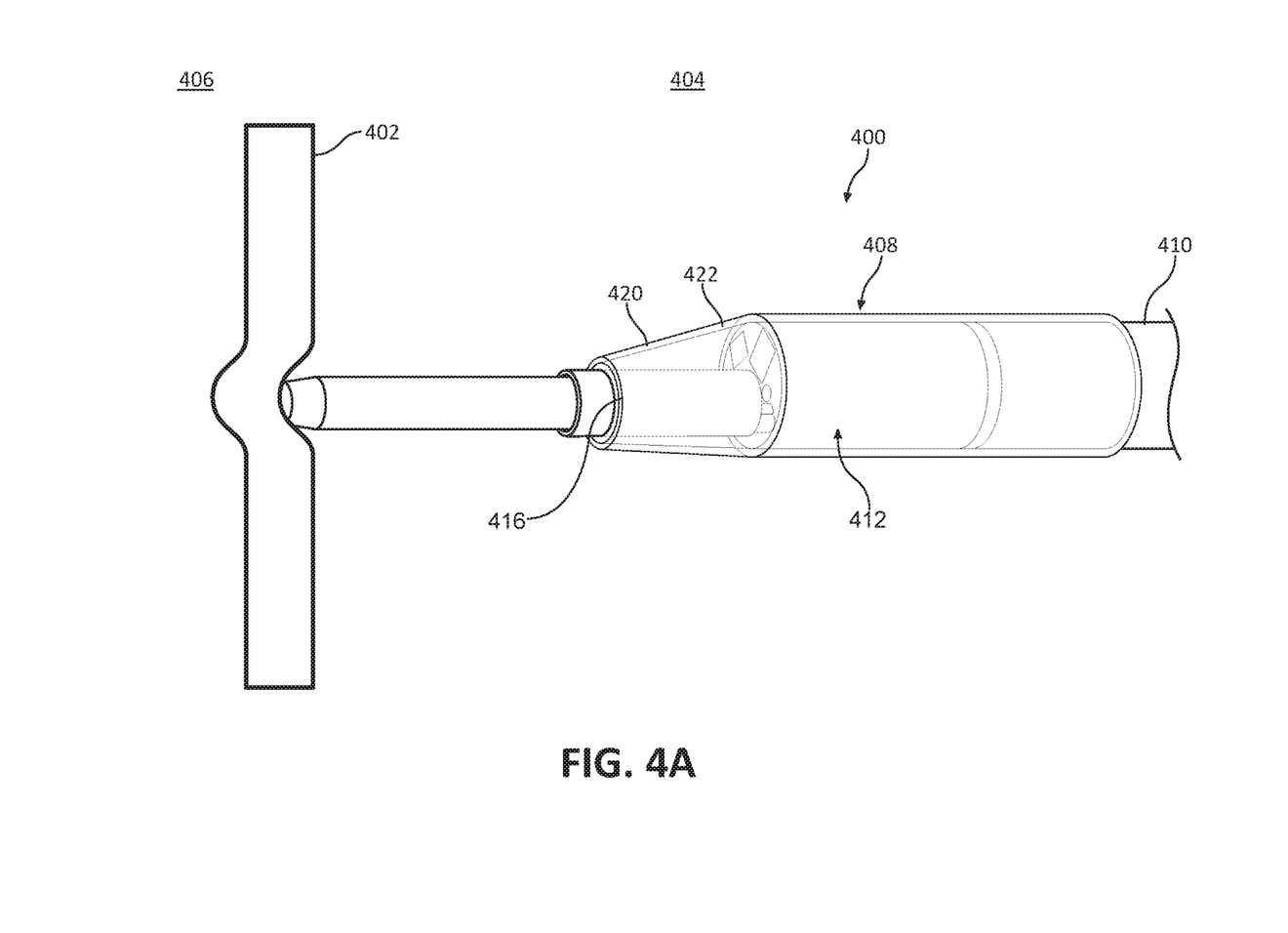
FIG. 4A shows an example apparatus for crossing a tissue region in a first configuration accordance with embodiments of the disclosure.

FIG. 4A shows an example apparatus 400 for crossing a tissue region 402 in a first configuration accordance with embodiments of the disclosure. The apparatus 400 is arranged on a first side 404 of the tissue region 402. The apparatus 400 is configured to cross the tissue region 402 from the first side 404 to the second side 406. The apparatus 400 may include a catheter 408 sized and shaped for vascular access and having an elongate body 410. FIGS. 4A-D show a distal end portion of the elongate body 410 of the apparatus 400. The apparatus 400 may include a tip section 412 arranged at a distal end of the elongate body 410. The apparatus 400 may also include a hydraulic actuator (not shown) coupled to a distal end of the catheter 408, as described above with reference to FIG. 1.

Figure 4B:
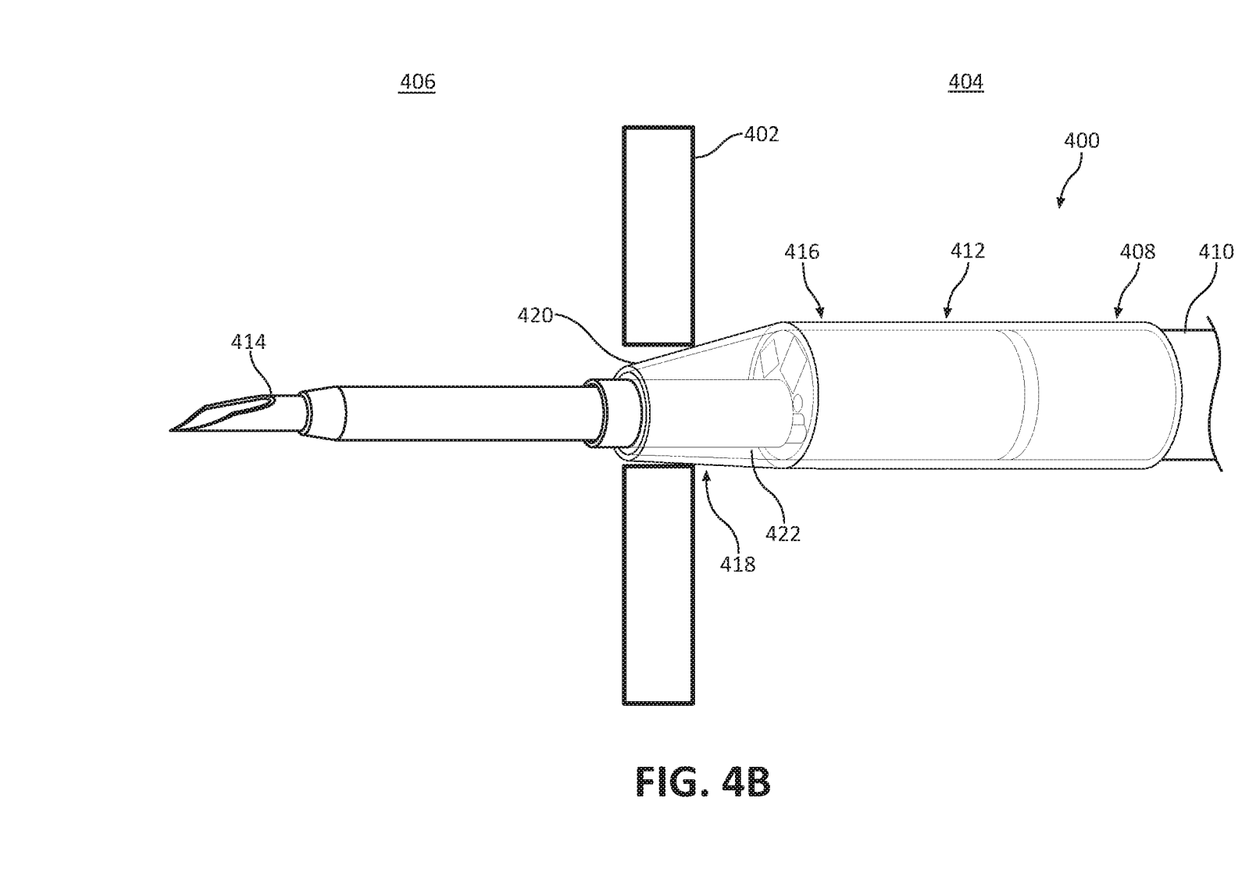
FIG. 4B shows the apparatus for crossing the tissue region, shown in FIG. 4A, in a second configuration accordance with embodiments of the disclosure.

The tip section 412 may include a needle portion 414 (shown in FIG. 4B) arranged at a distal end of the tip section 412 and a balloon 416 arranged proximally of the needle portion 414. The needle portion 414 (not shown in FIG. 4A) may be configured to puncture the tissue region 402 to create an opening as is shown in FIG. 4B in the first configuration of the apparatus 400. As is shown in FIG. 4A, the catheter 408, and more specifically the tip section 412, is arranged adjacent the tissue region 402 on the first side 404. An operator (physician) of the apparatus 400 or the hydraulic actuator may be configured to drive the needle portion 414 puncture the tissue region 402 to create the opening.

Figure 4C:
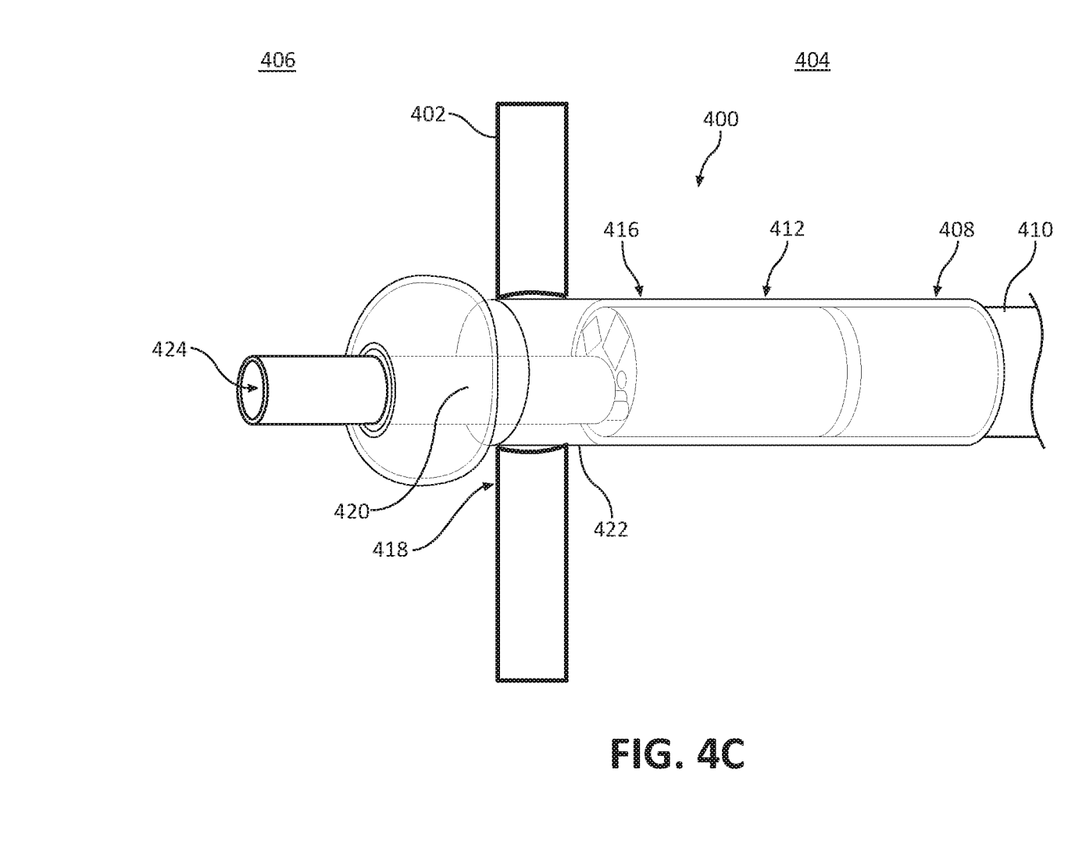
FIG. 4C shows the apparatus for crossing the tissue region, shown in FIGS. 4A-B, in a third configuration accordance with embodiments of the disclosure.

FIG. 4B shows the apparatus 400 for crossing the tissue region 402, shown in FIG. 4A, in a second configuration accordance with embodiments of the disclosure. In the second configuration, the needle portion 414 has punctured the tissue region 402 and created an opening 418 therein. In certain instances, the needle portion 414 may retract within a portion of the tip section 412 as is shown in FIG. 4C. Retraction of the needle portion 414 may be automatic such that the needle portion 414 functions a punch-type mechanism, or the needle portion 414 may be mechanically withdrawn by an operator (physician) of the apparatus 400. After the opening 418 is formed, the balloon 416 may be advanced within the opening 418.

In certain instances, the balloon 416 includes a first section 420 and a second section 422, with the first section 420 of the balloon 416 being configured to inflate prior to the second section 422. All or a portion of the second section 422 of the balloon 416 may be attached, bonded, or coupled to a portion of the tip section 412 and/or the elongate body 410 of the catheter 408.

As is shown in FIG. 4B, the balloon 416 is advanced within the opening 418 in the tissue region 402. In certain instances, the first section 420 of the balloon 416 is arranged in the opening 418. Subsequently, the opening 418 in the tissue region 402 is dilated by inflating the balloon 416 as is shown in FIG. 4C.

FIG. 4C shows the apparatus 400 for crossing the tissue region 402, shown in FIGS. 4A-B, in a third configuration accordance with embodiments of the disclosure. In the third configuration, the balloon 416 is in a partially inflated configuration. As shown in FIG. 4C, the opening 418 in the tissue region 402 is being dilated. In certain instances, the first section 420 of the balloon 416 dilates the opening 418 in the tissue region 402. The balloon 416 may inflate to a substantially spherical shape to dilate the opening 418 in the tissue region. In addition, the first section 420 of the balloon 416 may inflate in a biased manner such that a portion of the first section 420 of the balloon 416 on the second side 406 of the opening 418 in the tissue region 402 fills at a greater rate than a portion of the first section 420 of the balloon 416 on the first side 404 of the opening 418 in the tissue region 402. The first section 420 of the balloon 416 may include a taper that may assist in filling the balloon 416 in this manner. The first section 420 of the balloon 416 may cross to the second side 406 of the opening 406 while the second section 422 of the balloon 416 within the opening 418.

The tip section 412 and the catheter 408 may be passed through the opening 418 in the tissue region 402 after the opening 418 in the tissue region 402 has been dilated. In certain instances, the dilating the opening 418 in the tissue region 402 and passing of the tip section 412 through the opening 418 in the tissue region 402 may occur simultaneously. Filling the balloon 416, more specifically the first section 420 of the balloon 416, asymmetrically forces or drags the tip section 412 across the opening 418 in the tissue region 402 from the first side 404 to the second side 406. The first section 420 of the balloon 416 may apply pressure to the tissue region 402 on the second side 406 and pass the tip section 412 across the opening 418 in the tissue region 402. The balloon 416 may pass the tip section 412 across the opening 418 in the tissue region 402 in a gradual manner to avoid damaging structures arranged on the second side 406 of the tissue region 402.

In certain instances, the balloon 416 may be filled using a hydraulic actuator such as a peristaltic pump or syringe filled with saline. The hydraulic action created by the hydraulic actuator may be a function of inflating the first section 420 of the balloon 416 is arranged in the opening 418, as positioned within and partially through the opening 418 as shown in FIG. 4C. Inflating the first section 420 of the balloon 416 causes a hydraulic action that advances/pulls the tip section 412 across the opening 418. The hydraulic action allows for the tip section 412 to cross the opening 418 without need for the operator the catheter 408 through the opening 418.

Figure 4D:
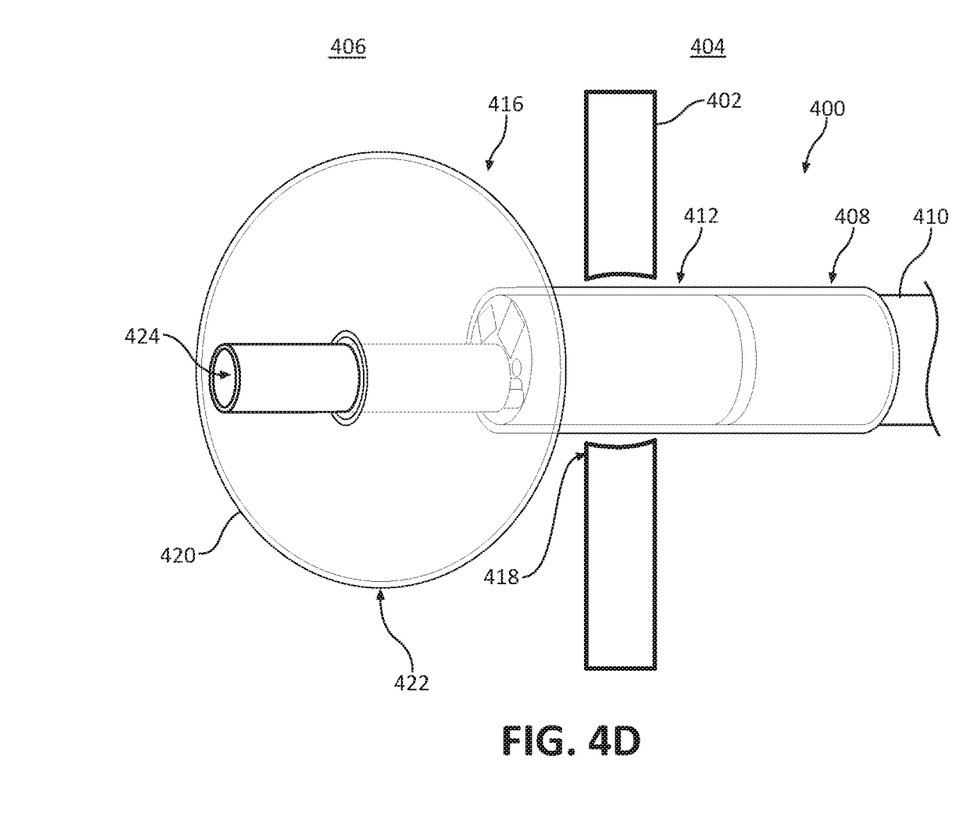
FIG. 4D shows the apparatus for crossing the tissue region, shown in FIGS. 4A-C, in a fourth configuration accordance with embodiments of the disclosure.

FIG. 4D shows the apparatus 400 for crossing the tissue region 402, shown in FIGS. 4A-C, in a fourth configuration accordance with embodiments of the disclosure. FIG. 4D shows the apparatus 400 for crossing the tissue region 402, shown in FIGS. 4A-C, in a fourth configuration accordance with embodiments of the disclosure. In the fourth configuration, the balloon 416 has dilated the opening 418 in the tissue region 402 and passed the tip section 412 therethrough. As shown in FIG. 4D, the balloon 416 is fully inflated after has dilating the opening 418 in the tissue region 402 and passing the tip section 412 therethrough. In the fully-inflated configuration, the balloon 416 may have a donut-like shape.

In certain instances, the apparatus 400 may include a working channel 424. The working channel 424 is configured to pass tools or other devices therethrough to the second side 406 of the tissue region 402. Thus, in addition to forming the opening 418 in the tissue region 402, dilating the opening 418 in the tissue region 402, and passing the apparatus 400 therethrough, the apparatus 400 may include the working channel 424 such that therapy (through devices or otherwise) may be arranged therethrough.

The illustrative components shown in FIGS. 4A-D are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 4A-D may be, in embodiments, integrated with various other components depicted therein (and/or components not illustrated), all of which are considered to be within the ambit of the disclosed subject matter. For example, the fluid source 114 and the hydraulic actuator 116 may be used in connection with apparatus 400. In addition, the tip section 412 may include different diameters as described with reference to FIG. 3.

Various modifications and additions may be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An apparatus for crossing a tissue region, the apparatus comprising:

a catheter sized and shaped for vascular access and including an elongate body extending between a proximal end and a distal end; and a tip section arranged at the distal end of the elongate body, the tip section including:

a needle portion arranged at a distal end of the tip section and configured to puncture the tissue region to create an opening therein and retract within the elongate body, and a balloon arranged proximally of the needle portion having a first section and a second section with at least a portion of the second section being coupled to the tip section, and the balloon is configured to dilate the opening in the tissue region and pass the tip section through the opening with the first section being configured to inflate prior to the second section; and a hydraulic actuator coupled to a proximal end of the catheter and configured to drive the needle portion through the tissue region and assist in the balloon passing the tip section through the opening.

2. The apparatus of claim 1, wherein at least a portion of the first section of the balloon comprises a first diameter and the second section of the balloon comprises a second diameter, the first diameter is less than the second diameter.

3. The apparatus of claim 2, wherein the first section tapers from the second diameter to the first diameter.

4. The apparatus of claim 1, wherein the balloon is configured to inflate to a substantially spherical shape to dilate the opening in the tissue region.

5. The apparatus of claim 1, wherein the balloon is configured to asymmetrically inflate.

6. The apparatus of claim 5, wherein a distal portion of the balloon is configured to inflate at a greater rate than a proximal section of the balloon thereby asymmetrically inflating the balloon.

7. The apparatus of claim 1, wherein the tip section comprises a first tip section having a first tip section diameter and a second tip section having a second tip section diameter, and the first tip section diameter is less than the second tip section diameter.

8. The apparatus of claim 7, further comprising a visualization element arranged at a distal end of the second tip section.

9. The apparatus of claim 7, further comprising a radiopaque marker arranged approximately at a transition between the first tip section and the second tip section.

10. The apparatus of claim 1, further comprising a hydraulic actuator configured to assist in passing the tip section through the opening in the tissue region.

11. The apparatus of claim 1, wherein the balloon is configured to concurrently dilate the opening in the tissue region and pass the tip section through the opening.

12. An apparatus for crossing a tissue region, the apparatus comprising:

a catheter sized and shaped for vascular access and including an elongate body extending between a proximal end and a distal end;

a tip section arranged at the distal end of the elongate body, the tip section including:

a needle portion arranged at a distal end of the tip section and configured to puncture the tissue region in a first configuration to create an opening therein and retract within the tip section in a second configuration, and a balloon arranged proximally of the needle portion and configured to dilate the opening in the tissue region and pass a portion of the tip section through the opening while in a partially inflated configuration; and a hydraulic actuator coupled to a proximal end of the catheter and configured to drive the needle portion through the tissue region and assist in the balloon passing the tip section through the opening.

13. The apparatus of claim 12, wherein the balloon is configured to concurrently dilate the opening in the tissue region and pass the portion of the tip section through the opening in the partially inflated configuration and transition to a fully inflated configuration after passing through the opening in the tissue.

14. The apparatus of claim 12, wherein the tip section comprises a first tip section having a first tip section diameter and a second tip section having a second tip section diameter, and the first tip section diameter is less than the second tip section diameter, and a first section of the balloon is arranged to surround the first tip section and a second section of the balloon is attached to the second tip section.

15. The apparatus of claim 14, wherein the first section of the balloon comprises a tapered diameter decreasing toward the distal end of the tip section.

16. A method for crossing a tissue region, the method comprising:

arranging a tip section of a catheter on the tissue region, the catheter being sized and shaped for vascular access and including an elongate body extending between a proximal end and a distal, the tip section including a needle portion and a balloon having a first section and a second section with at least a portion of the second section being coupled to the tip section;

puncturing the tissue region using the needle portion to create an opening using a hydraulic actuator coupled to a proximal end of the catheter to drive the needle portion through the tissue region;

retracting the needle portion within the tip section;

advancing the balloon within the opening in the tissue region;

dilating the opening in the tissue region by inflating the balloon with the first section being configured to inflate prior to the second section; and passing at least a portion of the tip section through the opening in the tissue region using the hydraulic actuator.

17. The method of claim 16, wherein dilating the opening and passing the at least a portion of the tip section through the opening occurs concurrently with inflation of the balloon.

18. The method of claim 16, wherein retracting the needle portion within the tip section occurs prior to advancing a first section of the balloon within the tissue region.

19. The method of claim 16, wherein dilating the opening in the tissue region by inflating the balloon comprises asymmetrically inflating the balloon section.

20. The method of claim 19, wherein asymmetrically inflating the balloon comprises inflating a distal portion of the balloon at a greater rate than a proximal section of the balloon.

* * * * *